United States Patent
Kurtz

(10) Patent No.: US 6,612,180 B1
(45) Date of Patent: Sep. 2, 2003

(54) DIELECTRICALLY ISOLATED PLASTIC PRESSURE TRANSDUCER

(75) Inventor: Anthony D. Kurtz, Ridgewood, NJ (US)

(73) Assignee: Kulite Semiconductor Products, Inc., Leonia, NJ (US)

(*) Notice: Subject to any disclaimer, the term of this patent is extended or adjusted under 35 U.S.C. 154(b) by 0 days.

(21) Appl. No.: 09/526,617

(22) Filed: Mar. 16, 2000

(51) Int. Cl.$^7$ ................................. G01L 9/00
(52) U.S. Cl. ........................................ 73/754
(58) Field of Search ..................... 73/754, 721, 727, 73/716, 720, 708, 715, 726; 257/419

(56) References Cited

U.S. PATENT DOCUMENTS

| | | | |
|---|---|---|---|
| 4,222,277 A | * 9/1980 | Kurtz et al. | 73/721 |
| 4,617,607 A | * 10/1986 | Park et al. | 73/724 |
| 4,644,797 A | * 2/1987 | Ichikawa et al. | 73/727 |
| 5,438,876 A | * 8/1995 | Lewis | 73/726 |
| 5,811,684 A | * 9/1998 | Sokn | 73/726 |
| 5,955,711 A | 9/1999 | Butala et al. | 200/6 BB |
| 5,955,771 A | * 9/1999 | Kurtz et al. | 257/419 |
| 5,973,590 A | 10/1999 | Kurtz et al. | 338/42 |
| 6,050,147 A | * 4/2000 | Viduya et al. | 73/756 |
| 6,058,782 A | * 5/2000 | Kurtz et al. | 73/708 |

* cited by examiner

*Primary Examiner*—Harshad Patel
(74) *Attorney, Agent, or Firm*—Duane Morris LLP

(57) ABSTRACT

A pressure sensing device suitable for medical use including: a dielectrically isolated sensor chip including a first wafer having first and second surfaces, a deflectable diaphragm formed therein and defining an active area of the sensor chip surrounded by an inactive area of the sensor chip, an electronic circuit formed on the first surface in the active area and being adapted to provide a signal indicative of an amount of deflection of the diaphragm, and a non-conductive coating on at least a portion of the second side; and, a plastic header including first and second ends, a recess in the first end and a plurality of electrically conductive pins extending from the recess through the header and out the second end; wherein, the sensor chip is secured within the recess of the plastic header such that the electronic circuit is in electrical contact with at least one of the pins.

16 Claims, 2 Drawing Sheets

DIELECTRICALLY ISOLATED PLASTIC PRESSURE TRANSDUCER

FIELD OF USE

The present invention relates generally to pressure sensing devices, and particularly to a pressure transducer adapted for medical use.

BACKGROUND OF INVENTION

It has long been known that pressure transducers used for monitoring blood pressure and the pressure of other body fluids or transducers that come into contact with biological fluids or materials must be intrinsically safe. That is to say, under no conditions can a high voltage be applied through such a body of fluid to a living body. Moreover, such transducers must be capable of being in a sterile condition immediately prior to use thereof.

In recent times it has been found advantageous to use a medical device only once and then to discard it, so as to prevent cross-contamination from one body to another. This implies the cost of such a device should be low enough to permit it being economically feasible to discard it after a single use. Therefore, it is an object of the present invention to provide such a pressure transducer.

SUMMARY OF INVENTION

A pressure sensing device suitable for medical use including: a dielectrically isolated sensor chip including a first wafer having first and second surfaces, a deflectable diaphragm formed therein and defining an active area of the sensor chip surrounded by an inactive area of the sensor chip, an electronic circuit formed on the first surface in the active area and being adapted to provide a signal indicative of an amount of deflection of the diaphragm, and a non-conductive coating on at least a portion of the second side; and, a plastic header including first and second ends, a recess in the first end and a plurality of electrically conductive pins extending from the recess through the header and out the second end; wherein, the sensor chip is secured within the recess of the plastic header such that the electronic circuit is in electrical contact with at least one of the pins.

DETAILED DESCRIPTION OF THE INVENTION

Basically, the device according to the present invention includes a plastic header containing a number of pins (four pins for a closed bridge and 5 pins for an open bridge). The pins protrude a short distance (about 0.005") from the top surface of the header and are several inches long in the back of the header. A dielectrically piezoresistive sensor is preferably utilized. A glass wafer containing a central aperture is secured to the inactive side of a silicon sensor wafer. The aperture is preferably approximately the same size as the deflectable diaphragm of the silicon wafer of the sensor. The exposed portion of the non-active side of the silicon wafer is coated with a nonconductive material such as silicon dioxide. Alternatively, this glass covering wafer could be omitted without effecting the sensor's performance.

A second glass wafer is affixed to the active side of the silicon wafer of the sensor. This second glass wafer includes apertures which are in contact with contact regions of the silicon wafer, and may be partially or totally filled with a conductive epoxy. The sensor is then affixed to the short header pins which are arranged to have a one-to-one correspondence to the contact apertures in the second glass wafer. It should be noted, if additional non-conducting layers are desired they may be applied or otherwise affixed to the inactive side of the sensor after it has been bonded to the header.

Figure 1:
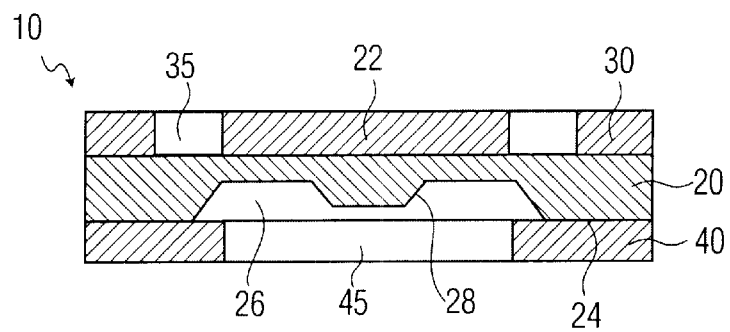
FIG. 1 illustrates a cross-section of a pressure sensing chip utilized according to a preferred form of the present invention.

Referring now to the figures, like references identify like elements of the invention. FIG. 1 illustrates a cross-section of a sensor chip 10 used according to a preferred form of the invention. The sensor chip 10 includes a sensor wafer 20 having a first covering member 30 and a second covering member 40 respectively coupled to its oppositely disposed surfaces 22 and 24. Formed on the surface 22 of the wafer 20 is a suitable pressure sensing structure 160 as will be discussed in relation to FIG. 4, which illustrates a preferred form of the same. The dielectrically isolated piezoresistive sensor chip 10 is preferably fabricated in accordance with the teachings of commonly assigned U.S. Pat. Nos. 5,955,771 entitled "SENSORS FOR USE IN HIGH VIBRATIONAL APPLICATIONS AND METHODS FOR FABRICATING SAME" issued Sept. 21, 1999 and 5,973,590 entitled "ULTRA THIN SURFACE MOUNT WAFER SENSOR STRUCTURES AND METHODS FOR FABRICATING SAME" issued Oct. 26, 1999, the entire disclosures of which are hereby incorporated by reference as if being set forth in their respective entireties herein.

Figure 4:
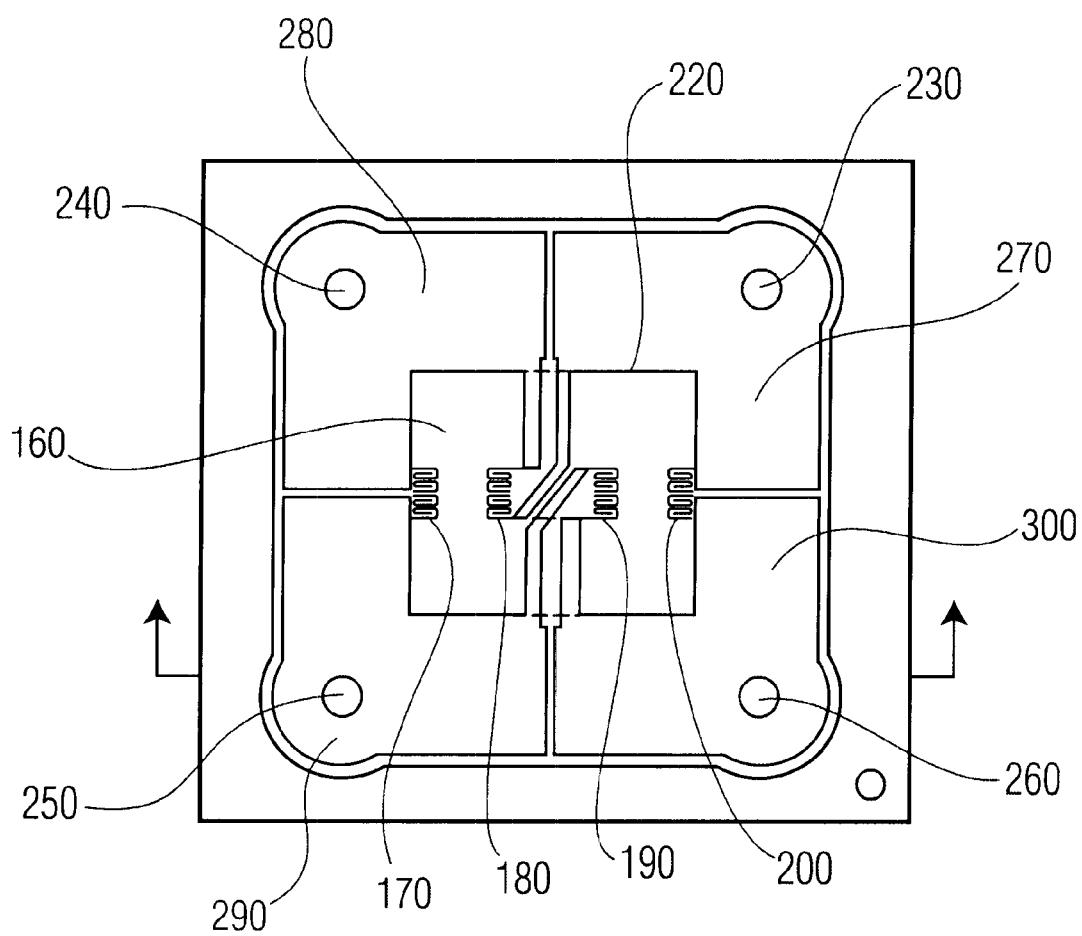
FIG. 4 illustrates a plan-view of a preferred circuit structure for the pressure sensing chip of FIG. 1.

Referring to FIG. 4, in the preferred form the circuit structure 160 takes the form of a piezoresistive bridge structure. It should of course be understood that other circuit plans could also be used as well. This pressure sensitive structure 160 is of the type having serpentine or tortuous piezoresistors 170, 180, 190, 200 composed of highly doped P+ silicon. Each piezoresistor 170 180, 190, 200 is essentially a variable resistor in one of four legs of a Wheatstone bridge circuit with each of the respective resistances varying in response to an applied force or pressure to the sensor 10. Referring also to FIG. 1, the portion 220 of the bridge structure 160 is generally referred to as the "active" area of the sensor 10 as it overlays a thinner region of the wafer 20, e.g. a diaphragm 28, that deflects upon the application of a pressure to the sensor. The areas of the sensor 10 that are external to the active area 220, e.g. around the periphery of the wafer 20, are termed the "non-active" areas for purposes of explanation.

Referring still to FIG. 4, for a closed bridge the four circuit nodes of the Wheatstone bridge consist of metalized electrical contacts 230, 240, 250, 260 located in the non-active areas of the transducer and formed on top of the P+ silicon. Interconnecting the contacts 230, 240, 250, 260 with the piezoresistors 170, 180, 190, 200 are electrical interconnections or "fingers" 270, 280, 290, 300 which are also formed of P+ silicon. It is noted that the contacts 230, 240, 250, 260 being formed on top of P+ silicon are conductive, as are the interconnections 270, 280, 290, 300 to allow ohmic contact between the piezoresistors 170, 180, 190, 200 and the contacts 230, 240, 250, 260. It should be understood, while the terms "electrical contacts", "interconnections" and "fingers" are used for convenience, these terms can each be considered to essentially be the electrical paths that electrically couple the piezoresistor elements 170, 180, 190, 200 with the contact areas 230, 240, 250, 260. The interconnections 270, 280, 290, 300 are wider than the piezoresistors 170, 180, 190, 200 to provide a low resistance path to the contacts 230, 240, 250, 260, while the long, tortuous lengths and narrow widths of the piezoresistors 170, 180, 190, 200 are designed to provide the desired resistances.

Referring again to FIG. 1, the wafer 20 includes a thinned portion which defines the deflectable diaphragm 28 which in turn defines the active area 220 of the structure 160 of FIG. 4. The diaphragm 28 defines a recessed area 26 within the wafer 20 which is aligned with the active area 220 of the sensor chip 10. Again, for purposes of explanation the side 22 of the wafer 20 having the structure 160 formed thereon, opposite to the recess 26, is referred to herein as the "active" side, while the oppositely disposed side 24 is referred to as the "inactive" side. To the inactive side 24 of the wafer 20 is sealed a glass wafer or covering member 40 which includes an aperture 45 with is preferably central to the deflecting portion of the diaphragm 28, e.g. active area 220, and hence accesses the recess 26. When the member 40 is coupled to the wafer 20 using any suitable means, the aperture 45 opens into the small, shallow depression or recess 26 being preferably approximately equal in size to deflecting diaphragm 28 which forms the active area 220. The portion of the non-active side 24 of the wafer 20 which is exposed by the aperture 45 is preferably coated with silicon-oxide or some other suitable non-conductive material as has been set forth. It should be clear that the glass-covering wafer 40 may alternatively be omitted without significantly effecting performance as long as the appropriate surfaces of the wafer 20 which will come into contact with biological material is still coated with a suitable non-conductive material.

Still referring to FIGS. 1 and 4, a second covering or glass member 30 is preferably sealed to the P+ fingers 270, 280, 290, 300 formed on the active side 22 of the wafer 20. The glass member 30 includes apertures 35 passing there through which align with the contact areas 230, 240, 250, 260 of the structure 160. The glass member 30 is preferably sealed to the wafer 20 using the method described in the before-identified, commonly assigned U.S. Pat. No. 5,973,590. It should be recognized any other suitable method for securing the member 30 to side 22 of the wafer 20 could be used though. The wafer 20 preferably is composed of silicon while the covering members 30 and 40 preferably are composed of a suitable glass.

Still referring to FIGS. 1 and 4, the apertures 35 though the second member 30 which access the contact regions 230, 240, 250, 260 of the sensor structure 160 are preferably at least partially or totally filled with a conductive epoxy to provide electrical conductivity through the covering member 30 for the contact areas 230, 240, 250, 260 of the circuit structure 160. Of course an alternative conductive medium such as a glass-metal frit could be used.

Figure 2:
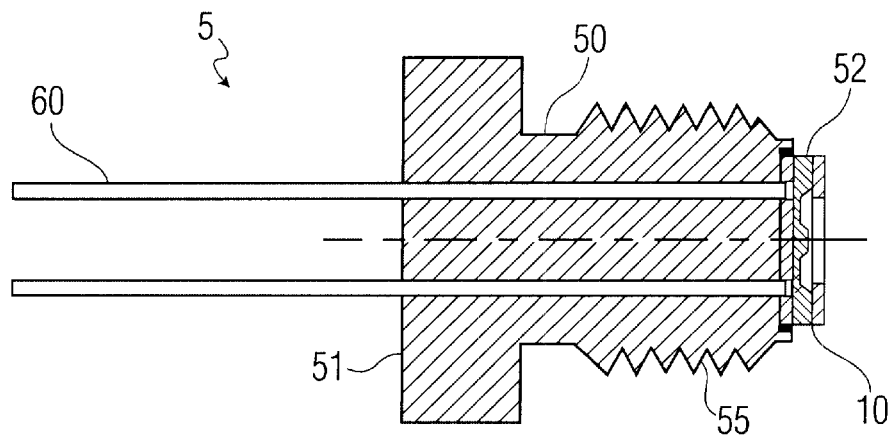
FIG. 2 illustrates a cross-section of the chip of FIG. 1 mounted to a plastic header according to a preferred form of the invention.

Referring now also to FIG. 2, therein is illustrated the sensor chip 10 of FIG. 1 mounted to a plastic header 50. Basically, as is illustrated in FIG. 2, the device 5 according to the present invention includes the leadless pressure sensing chip 10 of FIG. 1 coupled to a plastic header 50 which includes a number of pins 60 for providing electrically connectivity to the sensor chip 10. The header 50 is preferably made of a suitable plastic for medical use. The header 50 preferably includes a recess 52 in one end thereof having suitable dimensions to partially receive the sensor chip 10. The electrically insulated and conductive pins 60 run from the recess 52, through the header 50 and out the oppositely disposed back-side 51 of the header 50. The pins 60 provide electrical connectivity from the side 51 of the header 50 to the recess 52. The pins 60 protrude a short distance into the recess 52, preferably about 0.005 inches from the back of the recess 52 and are several inches long in the back-side 51 of the header 50. The header 50 further preferably includes threaded portion 55 suitable for attaching the assembly 5 to a port as will be discussed in relation to FIG. 3.

The sensor chip 10 is secured within the recess 52 of the header 50 such that the short end of header pins 60 are arranged and have a one-to-one correspondence to the contact apertures 35 in the second glass wafer 30. Accordingly they are in electrical contact with a conductive epoxy contained therein as has been set forth or by other means. It should be noted, that if additional non-conducting layers are desired they may be advantageously applied or otherwise affixed to the sensor after it has been bonded to the header, although they may be applied earlier in processing.

Figure 3:
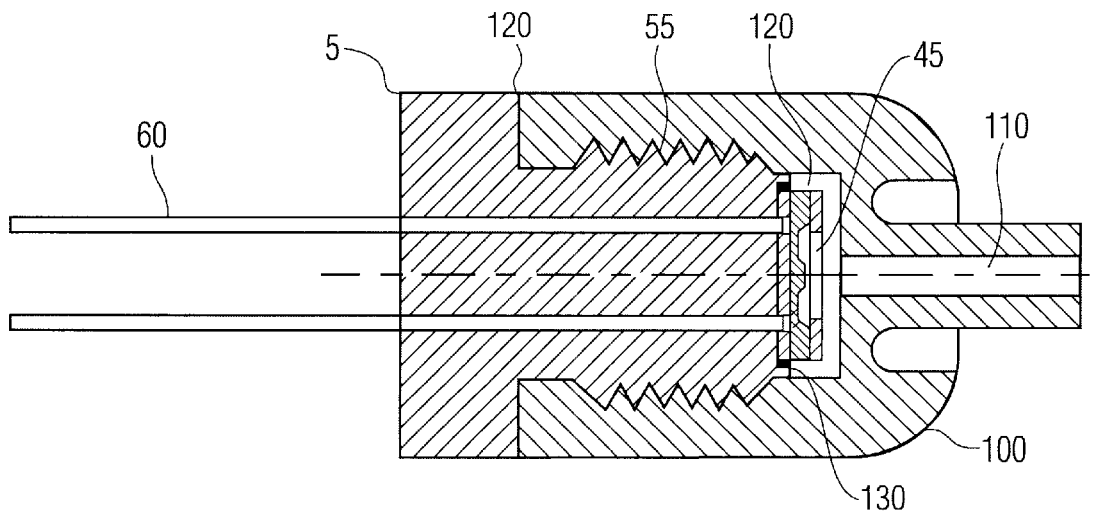
FIG. 3 illustrates a cross-section of the assembly of FIG. 2 further coupled to a port according to a preferred form of the invention.

Referring now to FIG. 3, therein is illustrated the device 5 according to the present invention coupled to port 100. The device 5 is preferably coupled to the port 100 using threaded portion 55 and a suitable epoxy seal 120. The port 100 includes a channel 110 (which is preferably readily coupleable with other suitable, conventional medical apparatus) being communicable with a recess 121 within the port 100. When the device 5 is coupled to the port 100, the sensor chip 10 and header 50 preferably form a rear wall 130 of the recess 121. Accordingly, when a media is introduced to the channel 110, it enters the recess 121 and is applied upon the portion of the wafer 20 having a non-conductive coating through the aperture 45 in the covering member 40. The pressure of the media introduced will cause the diaphragm 28 to deflect as is well known, causing the Wheatstone bridge structure 160 to generate an output signal indicative of the amount of deflection of the diaphragm 28 and hence the pressure of the media introduced. The pins or leads 60 can be used to sense this output.

An unanticipated advantage in using a plastic header in addition to its high dielectric strength and its imperviousness to biological fluids is the ability to mold a plastic piece into any desired shape at a relatively low cost. Thus the plastic header shown in FIG. 2 has a threaded section 55 along its outer periphery. In many medical applications it is desirable to affix a clear plastic pressure port 100 to the transducer 5 such that the media may be observed. Such a pressure port is shown in FIG. 3.

One can see that the combination of a "leadless" chip which in and of itself is inert to various biological fluids and electrically isolated from them together with an appropriately designed plastic header make possible the construction of a new-class of low cost medial transducers.

Although the invention has been described and pictured in a preferred form with a certain degree of particularity, it is understood that the present disclosure of the preferred form, has been made only by way of example, and that numerous changes in the details of construction and combination and arrangement of parts may be made without departing from the spirit and scope of the invention.

I claim:

1. A pressure sensing device suitable for medical use comprising:

a dielectrically isolated sensor chip including a wafer having first and second surfaces, a deflectable diaphragm formed therein and defining an active area of said sensor chip surrounded by an inactive area of said sensor chip, an electronic circuit formed on said first surface in said active area and providing a signal indicative of an amount of deflection of said diaphragm, and a non-conductive coating on at least a portion of said second surface; and, a plastic header including first and second ends, a recess in said first end and a plurality of electrically conductive pins extending from said recess through said header and out said second end, said plastic header comprising a plastic having high dielectric strength, imperviousness to biological fluids and being moldable to a desired shape, the header further including a threaded coupling portion for coupling a port to the header;

wherein, said sensor chip is secured within said recess of said plastic header such that said electronic circuit is in electrical contact with at least one of said pins.

2. The device of claim 1, wherein said electronic circuit includes a Wheatstone bridge piezoresistive circuit.

3. The device of claim 2, wherein said circuit further includes a plurality of conductive contact areas.

4. The device of claim 3, wherein each of said contact areas corresponds to one of said pins.

5. The device of claim 4, wherein each corresponding pin and contact area are in electrical contact with one another.

6. The device of claim 5, wherein said sensor chip further includes a first covering member secured to said first surface of said wafer and including a plurality of apertures passing therethrough, each of which is aligned with one of said contact areas.

7. The device of claim 6, wherein each of said apertures is filled with a conductive epoxy which electrically couples a corresponding one of said pins with the corresponding contact area.

8. The device of claim 6, further comprising a second covering member secured to said second surface of said wafer and including at least one aperture passing therethrough such that a pressure applied to said second covering member will act upon said portion of said second surface of said wafer having said non-conductive coating and cause said deflectable diaphragm to deflect.

9. The device of claim 8, wherein said port is made of a plastic suitable for medical use, said first and second covering members are made of a suitable glass and said wafer is made of silicon.

10. A pressure sensing device suitable for use as a medical device comprising:

a plastic header including first and second sides, at least a first recess in said first side and a plurality of electrically conductive paths between said recess and said second side, said plastic header comprising a plastic having high dielectric strength, imperviousness to biological fluids and being moldable to a desired shape, the header further including a threaded coupling portion;

a pressure sensor at least partially secured within said recess and including a plurality of electrical contacts each being respectively electrically coupled to a corresponding one of said conductive paths, the sensor having a surface at least partially coated with a non-conductive material; and a plastic port coupled to said plastic header by said threaded coupling portion of said header, and including a recess formed therein and a channel which opens to said recess for transporting a biological material to the at least partially coated surface of said sensor;

wherein pressure applied by the biological material to said at least partially coated surface of said sensor causes said sensor to generate a signal indicative of the pressure applied by the biological material.

11. The device of claim 10, wherein said plastic header and plastic port are respectively formed from a plastic suitable for medical use.

12. The device of claim 10, wherein said sensor further includes a first surface having a Wheatstone Bridge piezoresistive circuit formed thereon, and said first surface and said coated surface are disposed opposite from one another.

13. The device of claims 11, wherein said sensor includes:

a wafer having said at least partially coated surface, a second surface, a deflectable diaphragm formed therein, and a Wheatstone bridge piezoresistive circuit formed on said second surface over said deflectable diaphragm;

a first covering member secured to said second surface of said wafer and including a plurality of apertures passing therethrough; and, a second covering member secured to said at least partially coated surface of said wafer and including at least one aperture passing there through such that said at least one aperture is substantially adjacent to said deflectable diaphragm.

14. The device of claim 13, further comprising an electrically conductive material at least partially contained in said plurality of apertures in said first covering member.

15. The device of claim 14 wherein said wafer includes silicon and said first and second covering members includes glass.

16. The device of claim 15, wherein said portion of said sensor which is coated is exposable by said aperture in said second covering member.

* * * * *